United States Patent [19]

Levner

[11] 4,076,590

[45] Feb. 28, 1978

[54] **PROCESS FOR ENHANCING THE PRODUCTION OF ENTEROTOXIN BY *VIBRIO CHOLERAE***

[75] Inventor: Mark H. Levner, St. Davids, Pa.

[73] Assignee: American Home Products Corporation, New York, N.Y.

[21] Appl. No.: 686,617

[22] Filed: May 14, 1976

Related U.S. Application Data

[62] Division of Ser. No. 607,649, Aug. 25, 1975, Pat. No. 3,984,285.

[51] Int. Cl.[2] .............................................. C12D 13/02

[52] U.S. Cl. ...................................................... 195/96

[58] Field of Search .......................................... 195/96

[56] References Cited

U.S. PATENT DOCUMENTS 3,328,253 6/1967 Watanabe .............................. 195/96

OTHER PUBLICATIONS

Applied Microbiology, vol. 19, pp. 463-469, Mar. 1970.

*Primary Examiner*—Alvin E. Tanenholtz

*Attorney, Agent, or Firm*—Robert Wiser

[57] ABSTRACT

A process for increasing the production of enterotoxin by *Vibrio cholerae*, and enterotoxigenic strains of *Escherichia coli*, is disclosed. This process produces enhanced amounts of enterotoxin activity compared to amounts obtainable by practice of standard procedures.

1 Claim, No Drawings

PROCESS FOR ENHANCING THE PRODUCTION OF ENTEROTOXIN BY *VIBRIO CHOLERAE*

This is a division of application Ser. No. 607,649 filed Aug. 25, 1975, now U.S. Pat. No. 3,984,285.

BACKGROUND OF THE INVENTION

The devastating effects of the *Vibrio cholerae* produced enterotoxin, choleragen, on the human intestine are well-known, and have been documented in the literature [see for example, N. Hirschhorn et al., Sci. Am., 225, 15 (1971)]. Additionally, enterotoxin produced by certain strains of *Escherichia coli* has been implicated as being responsible for certain infant and travelers' diarrhea which is characterized by the "cholera syndrome", [see for example, S. L. Gorbach et al., J. Clin. Invest., 50, 881 (1971); R. B. Sack et al., J. Infect. Dis., 123, 378 (1971); H. L. DuPont et al., N. Engl. J. Med., 285, 1 (1971); The New York Times, Section 19, Page 1, June 1, 1975]. This syndrome is characterized by profuse "rice water" diarrhea leading to collapse and possibly to death.

Because the results of *V. cholerae* and enterotoxigenic *E. coli* infections are at the least very inconvenient and uncomfortable and at the worst can result in the death of the host, there is much ongoing research attempting to identify and purify the toxins presumed responsible for these effects in order that anti-toxins and/or toxoids may someday be made available to combat their effects. To date, choleragen has been purified and shown to be a protein consisting of two types of subunits [J. J. Lo Spalluto et al., Biochem. Biophys. Acta., 257, 158 (1972)] and *E. coli* produced enterotoxin has been shown to exist in heat-labile and heat-stable forms [C. L. Gyles, Ann. N. Y. Acad. Sci., 176, 314 (1971) and references cited therein] but *E. coli* enterotoxin has not yet been characterized as completely as choleragen. The heat-labile form however, has been shown to cross-react with choleragen antibody [D. R. Nalin et al., J. Inf. Diseases, 130, 595 (1974)], thus demonstrating that each antigen may be neutralized, and suggesting that their specific effects may be reduced or eliminated if the proper antitoxin is administered. Because *E. coli* enterotoxin cross-reacts with choleragen antibody, one might assume that these proteins possess some common structural features.

Taking into account this possible similarity in structure and because a *V. choleara* toxoid has been prepared, [Rappaport et al., Infect. and Immun., 9, 304 (1974)], one would expect that an *E. coli* toxoid can similarly be prepared.

Research in these areas related to *V. cholerae* and *E. coli* enterotoxin and their effects would, of course, be facilitated by the production and availability of increased amounts of the enterotoxins.

SUMMARY OF THE INVENTION

The invention sought to be patented in a principal process aspect resides in the concept of a process for producing *Escherichia coli* enterotoxin comprising growing an enterotoxigenic strain of *Escherichia coli* in the presence of lincomycin.

The invention sought to be patented in its first subgeneric process aspect resides in the concept of a process for producing *Escherichia coli* enterotoxin comprising growing *Escherichia coli* H197 [NRRL B-8104] in the presence of lincomycin.

The invention sought to be patented in its second subgeneric process aspect resides in the concept of a process for producing *Escherichia coli* enterotoxin comprising growing *Escherichia coli* H197 $Lin^r$ in the presence of lincomycin.

The invention sought to be patented in its third subgeneric process aspect resides in the concept of a process for producing *Escherichia coli* enterotoxin comprising growing *Escherichia coli* H10407 [NRRL B-8105] in the presence of lincomycin.

The invention sought to be patented in its fourth subgeneric process aspect resides in the concept of a process for producing *Escherichia coli* enterotoxin comprising growing *Escherichia coli* 711 (P307)[NRRL B-8106] in the presence of lincomycin.

The invention sought to be patented in its fifth subgeneric process aspect resides in the concept of a process for producing *Escherichia coli* enterotoxin comprising growth *Escherichia coli* 711 (P155)[NRRL B-8107] in the presence of lincomycin.

The invention sought to be patented in a second process aspect resides in the concept of a process for producing *Vibrio cholerae* enterotoxin comprising growing *Vibrio cholerae,* Inaba 569B [ATCC 25870] in the presence of lincomycin.

The invention sought to be patented in a third process aspect resides in the concept of a process for producing *Vibrio cholerae* enterotoxin comprising growing *Vibrio cholerae,* Inaba 569B $Lin^r$ in the presence of lincomycin.

DESCRIPTION OF THE INVENTION

The process of the invention comprises growing an enterotoxigenic strain of *Escherichia coli* or *Vibrio cholerae* Inaba 569B [ATCC 25870] and spontaneous mutant strains arising therefrom in a growth medium containing the antibiotic, lincomycin. It has been observed that when the chosen microorganism is allowed to grown in the presence of lincomycin, the amount of enterotoxin produced by the microorganism is greatly increased when compared to the amount normally produced. No analagous direct induction by an antibiotic agent of the production of a bacterial protein, which protein is apparently unrelated to the cell's resistance to the antibiotic, has previously been reported, and this finding is quite surprising and unexpected. No appreciable induction of enterotoxin production is observed when one substitutes kanamycin (another Streptomyces produced antibiotic) for lincomycin in the growth medium. Thus, the observed lincomycin induction of enterotoxin production is not a general phenomenon and appears to be peculiar to lincomycin.

The microorganisms contemplated by the invention are the enterotoxigenic strains of the genus *Escherichia coli,* the species *Vibrio cholerae* Inaba 569B, [ATCC 25870] and spontaneous mutants arising therefrom. Those skilled in the art will be familiar with the strains of *E. coli* which produce enterotoxin, for example several enterotoxigenic *E. coli* strains are disclosed in D. G. Evans et al., Infect. and Immun., 8, 731 (1973); R. B. Sack et al., J. Infect. Diseases, 123, 378 (1971); and references cited therein.

When practicing the invention, the chosen microorganism is grown in a proper nutrient medium [for example a yeast extract-supplemented casamino acids salts medium as described by D. J. Evans et al., Infect. Immunity, 8, 725 (1973)], in the presence of a suitable concentration of lincomycin. It will be obvious to those skilled in the art that the process of the invention must be carried out using a subinhibitory concentration of the antibiotic. The inhibitory concentration is that concentration of antibiotic at which there is substantially no growth of the microorganism. This concentration is readily ascertainable by one skilled in the art by, for example, the well-known serial dilution method, and will vary depending on the particular strain of bacterium being investigated. It will also be obvious to one skilled in the art that there will be a minimum concentration of lincomycin below which the increase in yield of enterotoxin, although presumably present, would be hardly perceptible and difficult to measure. This minimum concentration has been found to be about 10 μg/ml., for the strains that have been tested although no sharp demarcation point between increased enterotoxin production and normal enterotoxin production has been demonstrated to date. It is assumed that an increase in enterotoxin production occurs at lower concentrations than 10 μg/ml. of lincomycin but this increase, being very small, is not only difficult to measure, but of limited practical utility. Thus, the optimal concentration of lincomycin will depend on the strain of bacterium being used and will be readily ascertainable by one skilled in the art.

Thus, when an enterotoxigenic strain of *Escherichia coli* is utilized, the instant process has been found to proceed efficiently when the concentration of lincomycin in the growth medium is in the range from about 10 μg/ml. to about 500 μg/ml., and the preferred concentration for *E. coli* H197 $Lin^r$ being from about 100 μg/ml. to about 250 μg/ml.

When *Vibrio cholerae* Inaba 569B [ATCC 25870] is the microorganism utilized, the instant process has been found to proceed efficiently at lincomycin concentrations of from about 10 μg/ml., to about 30 μg/ml., and the preferred range of lincomycin concentration for *V. cholerae* Inaba 569B $Lin^r$ is from about 10 μg/ml. to about 60 μg/ml.

The above disclosed ranges of lincomycin concentration are those at which the instant process has been found to proceed efficiently; other concentrations of lincomycin are contemplated by the invention, the only critical limitation being that subinhibitory lincomycin concentrations must obviously be utilized. Thus, the lincomycin concentration as long as it is subinhibitory is not critical to the practice of the invention, and the disclosed preferred ranges should not serve to delimit the scope of the invention. The subinhibitory lincomycin concentration may vary depending on the particular microorganism being utilized, however the assessment of this concentration is within the skill of the art.

The practice of the instant process has been observed to produce an increase in enterotoxin production after as few as 12 hours of incubation and the most dramatic increase in enterotoxin production appears to occur after about 24 to about 48 hours of incubation.

One skilled in the art will appreciate that because of the nature of the process of the invention a certain period of time is required before the increased amounts of enterotoxin being produced may be measured. This period of time corresponds approximately to the time necessary for the bacterial cultures to reach the late exponential phase of growth.

Ideally, the incubation should not be allowed to proceed for longer than about 48 hours in order to facilitate culture "work-up" and isolation of the enterotoxin-containing culture fraction. Thus, it has been found that after about 48 hours the culture medium becomes more difficult to process due to, among other factors, cell lysis; however this is a manipulative problem common to all culture media and is not process related. Those skilled in the art will be familiar with this problem and will be able to best judge the ideal length of incubation time depending on the bacterial species and culture medium chosen. In a preferred embodiment of the instant invention, it has been found that a convenient balance between ease of culture "work-up" and increased enterotoxin production occurs between about 24 to about 48 hours after culture inoculation.

The length of time of incubation is thus not a critical aspect of the practice of the instant process.

The *Escherichia coli* produced enterotoxin has been shown to affect vascular permeability as does the *Vibrio cholerae* produced enterotoxin, choleragen, which permits assay by a rabbit skin test. The enterotoxin activity of the culture media is thus readily assayed by permeability factor (PF) activity [D. J. Evans et al., Infect. Immunity, 8, 725 (1973)].

By the practice of the instant invention it has been observed that spontaneous mutant strains, resistant to higher concentrations of lincomycin than the parent strain from which they arise, may be isolated. The mutants are obtained by several passages of the parent strain at increasing lincomycin concentrations. For purposes of the instant invention the notation "$Lin^r$" is used to connote a spontaneous mutant strain which has been obtained from a parent strain. Thus *Escherichia coli* H197 $Lin^r$ connotes a spontaneous mutant strain which has been obtained from *Escherichia coli* H197 [NRRL B-8104]. Further, it has been observed that the spontaneous mutant strains of *E. coli* are resistant to at least 250 μg/ml lincomycin while the isolated spontaneous mutant strain obtained from *Vibrio cholerae* Inaba 569B [ATCC 25870] (*Vibrio cholerae* Inaba 569B $Lin^r$) is resistant to a concentration of up to about 50 μg/ml lincomycin.

These spontaneous mutant strains have demonstrated an even greater increase in enterotoxin production when grown in the presence of lincomycin than the increase demonstrated by the parent strains from which these spontaneous mutants have originated.

Cultures of the parent strains of the subject microorganisms are on deposit in public culture collections and are permanently available to anyone who requests same. The culture collection and identifying numbers are in brackets, [], following the name of the corresponding microorganism. Thus *Vibrio cholerae* Inaba 569B [ATCC 25870] is available from the American Type Culture Collection
12301 Parklawn Drive
Rockville, Maryland 20852

The *Escherichia coli* parent strains are all available from the

Northern Regional Research Laboratories of the United States Department of Agriculture
Agricultural Research Service
Peoria, Illinois 61604

In order to isolate the enterotoxigenic lincomycin resistant mutant strains of the instant invention (those identified by the notation "$Lin^r$"), the parent enterotoxigenic strain is submitted to multiple passages at increasing lincomycin concentrations. One skilled in the art will recognize that this procedure involves incubating the parent enterotoxigenic strain in a suitable growth medium [for example a yeast extract-supplemented casamino acids salts medium as described by D. J. Evanset al., Infect. Immunity, 8, 725 (1973)] in the presence of a suitable concentration of lincomycin (for example from about 15 μg/ml. to about 75 μg/ml) and using the resultant culture to innoculate a second culture containing an increased concentration of lincomycin and repeating this process until the desired enterotoxigenic lincomycin resistant mutant strain has been obtained. One skilled in the art will be able to assess the number of sequential passages required to obtain an enterotoxigenic lincomycin resistant mutant strain from a particular enterotoxigenic parent strain. The number of passages required may vary depending, for example on the strain of enterotoxigenic parent strain utilized, however, it has been observed that from about 2 to about 8 sequential passages will be sufficient to allow isolation of a desired enterotoxigenic lincomycin resistant mutant strain froma particular enterotoxigenic parent strain. It has also been observed that the lincomycin concentrations present in the growth media may be increased by varying amounts for each successive passage. Thus in a preferred embodiment of the invention in which *Escherichia coli* H197 [NRRL B-8104] is utilized to produce *Escherichia coli* H197 $Lin^r$, four sequential passages are utilized using lincomycin concentrations of 50 μg/ml., 100 μg/ml., 150 μg/ml., and 250 μg/ml., respectively. Variations in the lincomycin concentrations as well as in the number of sequential passages performed may be required by, for example utilizing a different strain of parent enterotoxigenic bacterium, however, such variations are within the skill of the art and are contemplated by the invention.

As has been stated hereinabove, it has been observed that the spontaneous mutant strains of *E. coli* are resistant to at least 250 μg/ml. lincomycin while the isolated spontaneous mutant strain obtained from *Vibrio cholerae* Inaba 569B [ATCC 25870] (*Vibrio cholerae* Inaba 569B $Lin^r$) is resistant to a concentration of up to about 50 μg/ml. lincomycin.

The following examples illustrate the best mode contemplated by the inventor for carrying out the process of the invention.

EXAMPLE I

Overnight cultures grown in 2% (w/v) Bacto-peptone®, 0.5% (w/v) NaCl at 37° without aeration were diluted 1:1000 into 40 ml yeast extract-supplemented casamino acids-salts medium [D. J. Evans et al., Infect. Immunity, 8, 725 (1973)], containing lincomycin at various concentrations, and shakes vigorously in 500 ml Erlenmeyer flasks at 37° for 48 hours. Peptone medium for lincomycin-resistant strains also contained lincomycin at 250 μg/ml (various *E. coli* $Lin^r$ strains) or 50 μg/ml (*V. cholerae* 569B $Lin^r$). Aliquots of 48 hour cultures were centrifuged, and supernatants filtered through 0.22 mμ Millipore filters prior to assay for vascular permeability factor (PF) by rabbit skin test, as described by Evans et al., Infect. Immunity, 8, 725 (1973). PF activity is expressed as the dilution factor at which a 0.10 ml sample gave 16 $mm^2$ blueing, estimated by interpolation of data plotted as log (dilution factor) vs. log (avg. diam. blueing)$^2$. Each figure is the average of data obtained with two rabbits; 2- to 3-fold variations in PF activity have been observed in multiple repetitions of all experiments, but significant increases in the presence of lincomycin have invariably been obtained.

| Experiment | Bacteria | Lincomycin(μg/ml) | PF Activity |
|---|---|---|---|
| 1 | E. coli H197 [NRRL B-8104] | 0 | <100 |
| | E. coli H197 [NRRL B-8104] | 10 | 280 |
| | E. coli H197 [NRRL B-8104] | 30 | 730 |
| 2 | E. coli H197 $Lin^r$ | 0 | <100 |
| | E. coli H197 $Lin^r$ | 30 | 390 |
| | E. coli H197 $Lin^r$ | 100 | 2900 |
| | E. coli H197 $Lin^r$ | 500 | 2500 |
| 3 | E. coli H10407 [NRRL B-8105] | 0 | 25 |
| | E. coli H10407 [NRRL B-8105] | 50 | 80 |
| | E. coli 711 (P307)[NRRL B-8106] | 0 | 32 |
| | E. coli 711 (P307)[NRRL B-8106] | 50 | 400 |
| | E. coli 711 (P155)[NRRL B-8107] | 0 | 11 |
| | E. coli 711 (P155)[NRRL B-8107] | 50 | 180 |
| 4 | V. cholerae Inaba 569B [ATCC 25870] | 0 | $1.3 \times 10^5$ |
| | V. cholerae Inaba 569B $Lin^r$ | 0 | $5.3 \times 10^4$ |
| | V. cholerae Inaba 569B $Lin^r$ | 50 | $1.2 \times 10^7$ |

EXAMPLE II

Isolation of *Escherichia coli* H197 $Lin^r$

The yeast extract-containing medium of Example I, containing lincomycin at 50 μg/ml., was inoculated with *E. coli* H197 [NRRL B-8104], and incubated overnight at 37° C. with aeration. This culture was then used to inoculate a second culture containing 100 μg/ml. lincomycin, which was then incubated overnight. Two more sequential passages, with lincomycin at 150 and 250 μg/ml., respectively, were performed, and appropriate dilutions of the last culture were plated on medium containing 2% (W/V) agar and 250 μg/ml. lincomycin. The plates were incubated overnight at 37° C; several of the resulting single colonies were purified by a second passage on such plates. All clones so obtained were stably resistant to lincomycin at 250 μg/ml.

The subject matter which the applicant regards as his invention is particularly pointed and distinctly claimed as follows:

1. A process for producing *Vibrio cholerae* enterotoxin comprising growing *Vibrio cholerae* Inaba 569B [ATTC 25870] in the presence of lincomycin.

* * * * *